United States Patent
Sick et al.

(10) Patent No.: US 10,548,632 B2
(45) Date of Patent: Feb. 4, 2020

(54) SUBCUTANEOUS IMPLANT INTEGRATED INSTRUMENT

(71) Applicant: Cardiac Pacemakers, Inc., St. Paul, MN (US)

(72) Inventors: Kathryn Sick, Shoreview, MN (US); Troy Ehle, Shoreview, MN (US); David P. Stieper, North Branch, MN (US); Serge Dubeau, Plymouth, MN (US); Tyler Thompson, St. Michael, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 99 days.

(21) Appl. No.: 15/486,234

(22) Filed: Apr. 12, 2017

(65) Prior Publication Data

US 2017/0296229 A1 Oct. 19, 2017

Related U.S. Application Data

(60) Provisional application No. 62/322,213, filed on Apr. 13, 2016.

(51) Int. Cl.
*A61B 17/34* (2006.01)
*A61B 17/32* (2006.01)

(52) U.S. Cl.
CPC .......... *A61B 17/3468* (2013.01); *A61B 17/32* (2013.01); *A61B 2017/320044* (2013.01); *A61B 2017/320056* (2013.01)

(58) Field of Classification Search
CPC .......... A61B 17/3468; A61B 17/32093; A61B 17/32; A61B 2017/320056; A61B 2017/320044; A61B 2017/347; A61B 2017/348; A61M 37/0069
See application file for complete search history.

(56) References Cited

U.S. PATENT DOCUMENTS

| | | | |
|---|---|---|---|
| 5,304,119 A | 4/1994 | Balaban et al. | |
| 6,939,318 B2 | 9/2005 | Stenzel | |
| 10,052,489 B2 | 8/2018 | Katra et al. | |
| 2010/0331868 A1* | 12/2010 | Bardy | A61M 37/0069 606/167 |
| 2011/0184449 A1 | 7/2011 | Lubock et al. | |
| 2014/0276928 A1 | 9/2014 | Vanderpool et al. | |
| 2016/0331398 A1 | 11/2016 | Foster et al. | |

OTHER PUBLICATIONS

International Search Report and Written Opinion issued in PCT/US2017/027278, dated Jul. 7, 2017, 10 pages.
International Search Report and Written Opinion issued in PCT/US2017/027279, dated May 19, 2017, 14 pages.
International Preliminary Report on Patentability issued in PCT/US2017/027278, dated Oct. 25, 2018, 7 pages.
International Preliminary Report on Patentability issued in PCT/US2017/027279, dated Oct. 25, 2018, 9 pages.

* cited by examiner

*Primary Examiner* — Erich G Herbermann
(74) *Attorney, Agent, or Firm* — Faegre Baker Daniels, LLP

(57) ABSTRACT

Aspects of the present disclosure are directed toward apparatuses, systems, and methods that comprise an introducer apparatus for facilitating subcutaneous implantation of a medical device. In certain instances, the apparatus may include a housing, an inserter configured to pass the medical device through the housing, and a tunneler configured to form a subcutaneous pocket for the medical device.

13 Claims, 9 Drawing Sheets

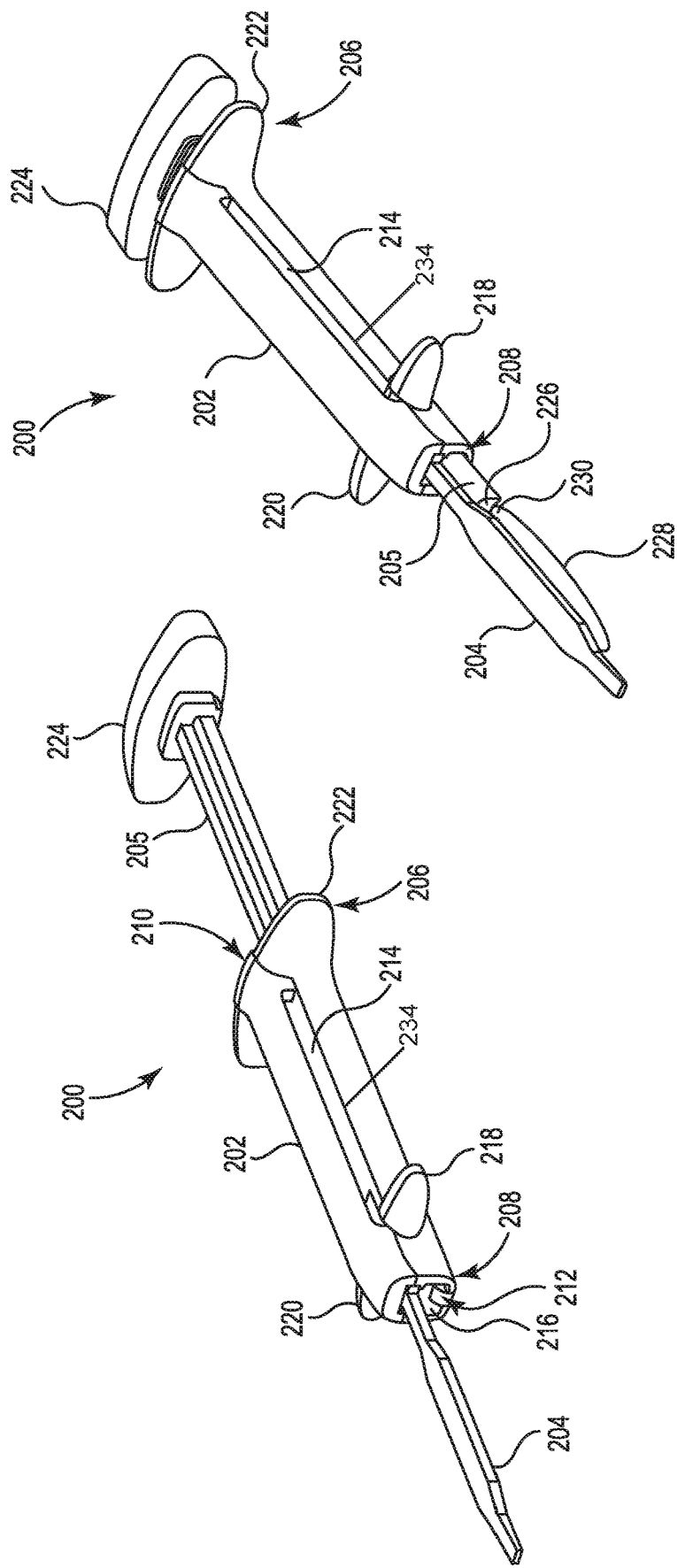

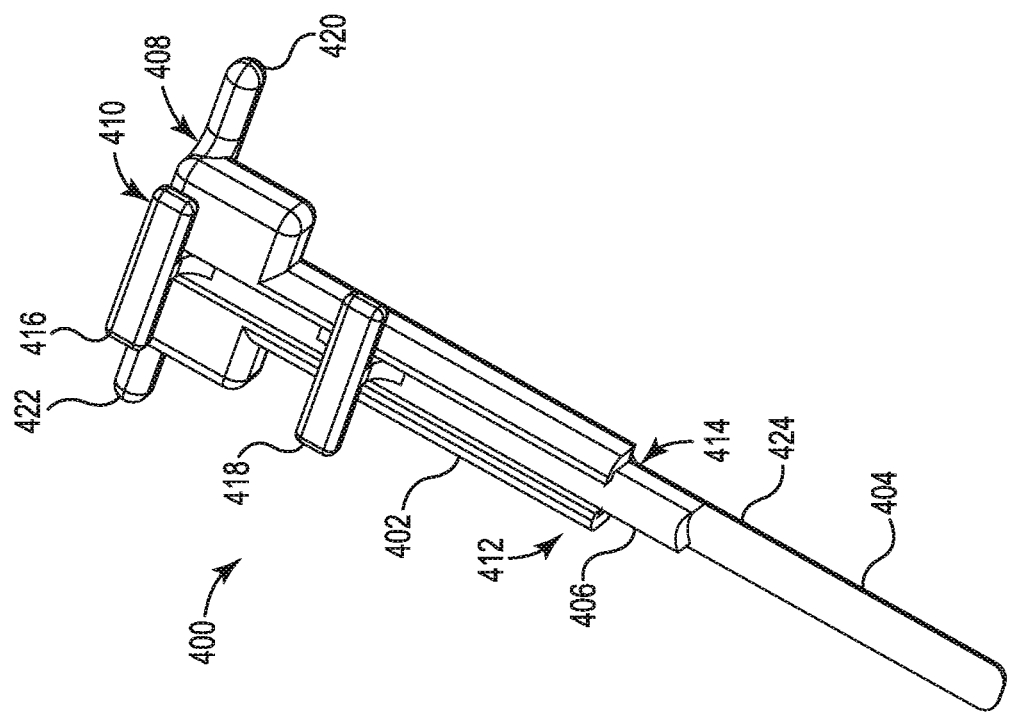

SUBCUTANEOUS IMPLANT INTEGRATED INSTRUMENT

CROSS-REFERENCE TO RELATED APPLICATION

This application claims priority to Provisional Application No. 62/322,213, filed Apr. 13, 2016, which is herein incorporated by reference in its entirety.

TECHNICAL FIELD

The present disclosure relates to medical devices and methods for creating a pocket in a patient for an implantable medical device. More specifically, the disclosure relates to devices and methods for facilitating implantation of the implantable medical device under the patient's skin.

BACKGROUND

Medical devices may be implanted subcutaneously under a patient's skin with relatively little intervention and without deeply positioning the device in the patient's body. Positioning of the medical device may be difficult due to high insertion forces necessary to manipulate the medical device and form a pocket for the device under the patient's skin. Improperly positioning functional aspects of the device may result in poor performance. This may include forming a pocket that is too large for the medical device, or forming a pocket having improper dimensions. In addition, improper pocket formation may result in difficult placement of the implantable medical device during the operation and/or the implantable medical device being ejected prior to sealing the pocket (e.g., stitching the incision). Further, improper pocket formation may result in an implanted device being ejected from a patient as a result of the patient's normal movement. Thus, there is a need for an introducer device that allows for improved pocket formation and positioning of an implantable medical device within the pocket.

SUMMARY

In Example 1, an introducer apparatus for facilitating subcutaneous implantation of a medical device, the apparatus including: a housing having a proximal end and a distal end, the housing defining at least one distal opening at or adjacent to the distal end; an inserter configured to pass the medical device through the at least one distal opening of the housing; and a tunneler configured to extend distally of the housing, the tunneler being configured to be moveable relative to the housing.

In Example 2, the apparatus of Example 1, wherein the inserter is configured to be moveable through a proximal opening of the housing and the at least one distal opening of the housing.

In Example 3, the apparatus of Example 2, wherein the housing includes a first channel extending along a length of the housing proximally from the at least one distal opening, and a second channel extending between the proximal opening and the at least one distal opening along the length of the housing, and the tunneler is configured to move within the first channel, and the inserter is configured to move within the second channel.

In Example 4, the apparatus of Example 3, wherein the inserter is distinct from and configured to disengage from the housing.

In Example 5, the apparatus of any of Examples 2-4, wherein the housing includes lateral openings on opposing sides of the housing and extending along a portion of the length of the housing, and the tunneler includes gripping portions coupled thereto and extending laterally through the lateral openings, the gripping portions being configured to facilitate movement of the tunneler within the first channel.

In Example 6, the apparatus of Example 3, wherein the inserter includes a first portion and a second portion, the second portion being configured to engage the medical device and pass the medical device through the at least one distal opening of the housing.

In Example 7, the apparatus of Example 6, wherein the first portion of the inserter is configured to engage the second portion of the inserter to move the second portion and the first portion together within the second channel in a first configuration, extend the second portion of the inserter through the at least one distal opening and engage a portion of the tunneler in a second configuration, and retract the tunneler from the at least one distal opening along the first channel in a third configuration.

In Example 8, the apparatus of Example 7, wherein the second portion of the inserter includes a depth limiter configured to lock the second portion of the inserter within the at least one distal opening in the second configuration.

In Example 9, the apparatus of any of Examples 7-8, wherein the tunneler extends through the at least one distal opening in the first configuration.

In Example 10, the apparatus of any of Examples 7-9, wherein the housing includes a compartment within the housing configured to releasably hold the medical device.

In Example 11, the apparatus of Example 10, wherein the medical device is releasably held within the compartment in a loading configuration, and the first portion of the inserter is configured to retract the second portion of the inserter to move the first portion and the second portion together toward the proximal opening from the loading configuration, and the medical device releases from the compartment into the second channel.

In Example 12, the apparatus of any of Example 1-11, wherein the housing includes a handle arranged at the proximal portion of the housing.

In Example 13, the apparatus of any of Example 1-12, wherein the tunneler includes a central portion and end portions surrounding the central portion, wherein the central portion includes a greater width than at least one of the end portions of the tunneler.

In Example 14, the apparatus of Example 13, wherein the tunneler includes a distal tip having a depth that is less than a depth of the central portion and the end portions of the tunneler.

In Example 15, the apparatus of Example 14, wherein the distal tip includes a taper lessening at least one of the depth and width of the distal tip.

In Example 16, an introducer apparatus for facilitating subcutaneous implantation of a medical device, the apparatus including: a housing having a proximal end and a distal end, the housing defining at least one distal opening at or adjacent to the distal end; an inserter configured to pass the medical device through the at least one distal opening of the housing and to extend through the proximal opening and the at least one distal opening of the housing; and a tunneler configured to extend distally of the housing to form a subcutaneous pocket in tissue of a patient for implantation of the medical device, the tunneler being moveable relative to the housing.

In Example 17, the apparatus of Example 16, wherein the housing includes a first channel extending along a length of the housing proximally from the at least one distal opening, and a second channel extending between the proximal opening and the at least one distal opening along the length of the housing, and the tunneler is configured to move within the first channel, and the inserter is configured to move within the second channel.

In Example 18, the apparatus of Example 17, wherein the housing includes lateral openings on opposing sides of the housing and extending along a portion of the length of the housing, and the tunneler includes gripping portions coupled thereto and extending laterally through the lateral openings, the gripping portions being configured to facilitate movement of the tunneler within the first channel.

In Example 19, the apparatus of Example 17, wherein the inserter includes a first portion and a second portion, the second portion being configured to engage the medical device and pass the medical device through the at least one distal opening of the housing.

In Example 20, the apparatus of Example 19, wherein the first portion of the inserter is configured to engage the second portion of the inserter to move the second portion and the first portion together within the second channel in a first configuration, extend the second portion of the inserter through the at least one distal opening and engage a portion of the tunneler in a second configuration, and retract the tunneler from the at least one distal opening along the first channel in a third configuration.

In Example 21, the apparatus of Example 20, further a compartment within the housing configured to releasably hold the medical device.

In Example 22, the apparatus of Example 21, wherein the medical device is releasably held within the compartment in a loading configuration, and the first portion of the inserter is configured to retract the second portion of the inserter to move the first portion and the second portion together toward the proximal opening from the loading configuration, and the medical device releases from the compartment into the second channel.

In Example 23, a system including: a medical device; and an introducer apparatus for facilitating subcutaneous implantation of the medical device, the apparatus including: a housing having a proximal end and a distal end, and including at least one distal opening at or adjacent to the distal end, an inserter configured to pass the medical device through the at least one distal opening of the housing and to extend through the proximal opening and the at least one distal opening of the housing, and a tunneler configured to form a subcutaneous pocket for the medical device and extend distally of the housing for insertion of the medical device in a first configuration, and retract relative to the first position in a second configuration.

In Example 24, the system of Example 23, wherein the housing includes a first channel extending along a length of the housing proximally from the at least one distal opening, and a second channel extending between the proximal opening and the at least one distal opening along the length of the housing, and the tunneler is configured to move within the first channel, and the inserter is configured to move within the second channel.

In Example 25, the system of Example 24, wherein the housing includes lateral openings on opposing sides of the housing and extending along a portion of the length of the housing, and the tunneler includes gripping portions coupled thereto and extending laterally through the lateral openings, the gripping portions being configured to facilitate movement of the tunneler within the first channel between the first configuration and the second configuration.

In Example 26, the system of Example 23, wherein the inserter includes a first portion and a second portion, the second portion being configured to engage the medical device and pass the medical device through the at least one distal opening of the housing.

In Example 27, the system of Example 26, wherein the first portion of the inserter is configured to engage the second portion of the inserter to move the second portion and the first portion together within the second channel in a first configuration, extend the second portion of the inserter through the at least one distal opening and engage a portion of the tunneler in a second configuration, and retract the tunneler from the at least one distal opening along the first channel in a third configuration.

In Example 28, the system of Example 23, further including a compartment within the housing configured to releasably hold the medical device.

In Example 29, the system of Example 23, wherein the tunneler includes a central portion and end portions surrounding the central portion, wherein the central portion includes a greater width than at least one of the end portions of the tunneler.

In Example 30, the system of Example 23, wherein the tunneler includes a distal tip having a depth that is less than a depth of the central portion and the end portions of the tunneler.

In Example 31, a method of implanting an implantable medical device using an introducer apparatus, the method including: making an incision in a patient's skin; positioning the introducer within the incision, the introducer comprising: a housing having a proximal end and a distal end, and including at least one distal opening arranged at or adjacent to the distal end, a tunneler extending distally from the housing, and an inserter; creating a subcutaneous pocket in the tissue of the patient for the medical device using the tunneler; ejecting the medical device through the at least one distal opening of the housing into the subcutaneous pocket via the inserter; and retracting the tunneler relative to the housing to remove the tunneler from the pocket while leaving the medical device in the subcutaneous pocket.

In Example 32, the method of Example 31, wherein the tunneler is moveable relative to the housing.

In Example 33, the method of Example 32, further including holding the medical device within the pocket using the inserter during the step of removing the tunneler from the pocket.

In Example 34, the method of Example 31, wherein the inserter is removable from and moveable relative to the housing.

In Example 35, the method of Example 34, further including holding the medical device within the pocket using the inserter.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE DRAWINGS

FIG. 2B is a perspective view of the illustrative introducer apparatus, as shown in FIG. 2A, in an initial configuration and including an inserter, in accordance with embodiments of the disclosure.

FIG. 2C is a perspective view of the illustrative introducer apparatus, as shown in FIGS. 2A-B, in a first configuration, in accordance with embodiments of the disclosure.

FIG. 4A is a perspective view of another illustrative introducer apparatus for facilitating subcutaneous implantation of a medical device, in accordance with embodiments of the disclosure.

Figure 1:
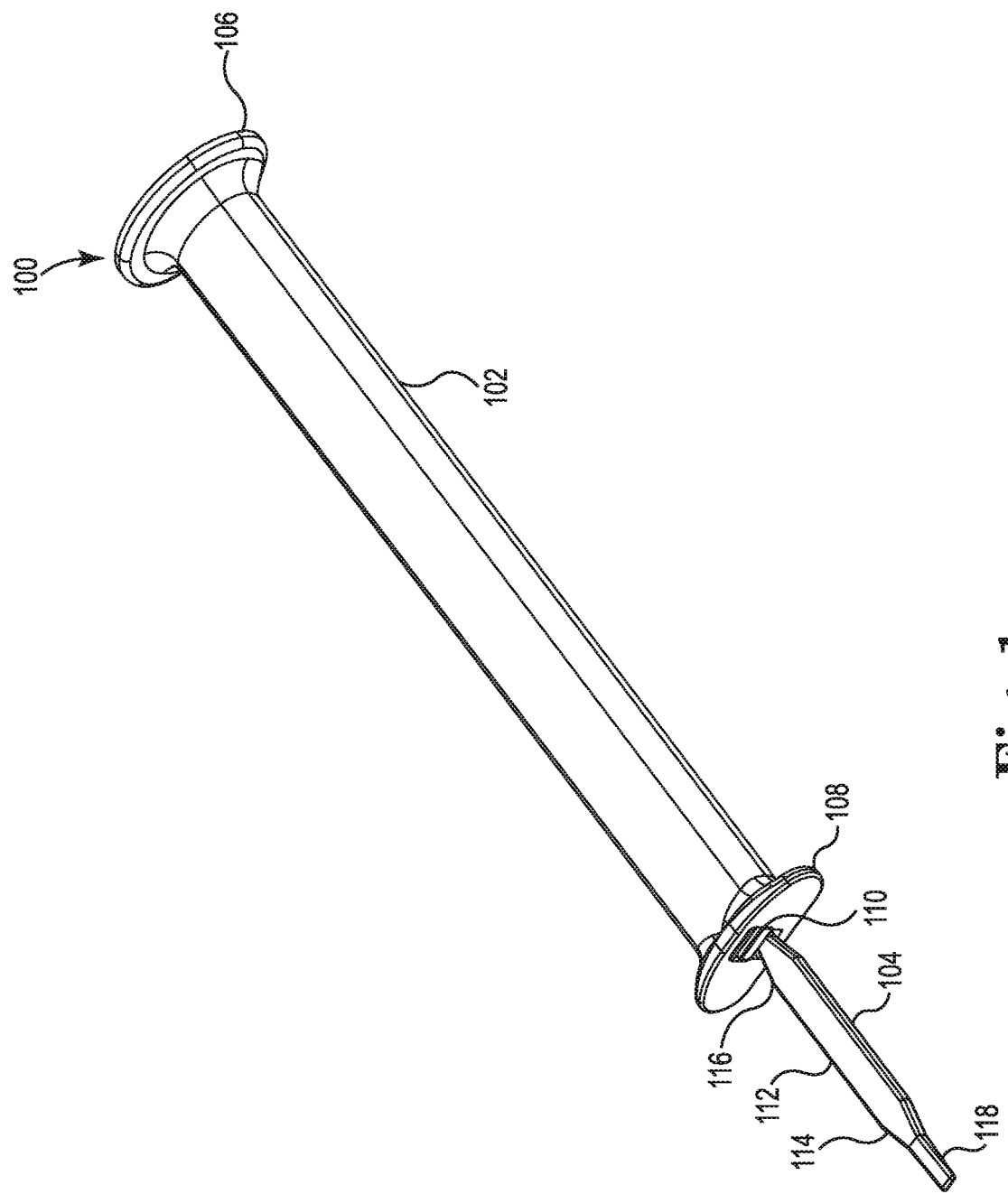
FIG. 1 is a perspective view of an illustrative introducer apparatus for a medical device, in accordance with embodiments of the disclosure.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to ranges of measurements (such as those disclosed immediately above), "about" and "approximately" may be used, interchangeably, to refer to a measurement, position, or arrangement, that includes the stated measurement, position, or arrangement and that also includes any measurement, positions, or arrangements that are reasonably close to the stated measurement, position, or arrangement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, positions, or arrangements, adjustments made to optimize performance and/or structural parameters in view of differences in measurements, positions, or arrangements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various steps disclosed herein unless and except when explicitly referring to the order of individual steps. Additionally, a "set" or "group" of items (e.g., inputs, algorithms, data values, etc.) may include one or more items, and, similarly, a subset or subgroup of items may include one or more items.

DETAILED DESCRIPTION

FIG. 1 is a perspective view of an illustrative introducer apparatus 100 for a medical device (not shown), in accordance with embodiments of the disclosure. The introducer apparatus 100 includes a housing 102 and a tunneler 104. The housing 102 includes a proximal end 106 and a distal end 108. Each of the proximal end 106 and the distal end 108 of the housing 102 may include, respectively, a proximal opening (not shown) and a distal opening 110 arranged, respectively, at or adjacent to the proximal end 106 and the distal end 108. The distal opening 110 (and the housing 102) may be formed or manufactured to accommodate medical devices of various sizes. The implantable medical device may be loaded into the housing 102 via either of the proximal opening or the distal opening 110.

The tunneler 104, as shown in FIG. 1, is arranged at, and extends from, the distal end 108 of the housing 102. In certain instances, the introducer apparatus 100 may be configured for facilitating subcutaneous implantation of the medical device. Consistent therewith, the tunneler 104 may be configured to form a subcutaneous pocket for the medical device. In creating the subcutaneous pocket in a patient, an incision may be made in the patient's skin. The incision may be made by a separate device, such as a scalpel. After the incision is made, the tunneler 104 may be manipulated within the patient through the incision. In certain instances, the user may rotate the introducer apparatus 100 to create the pocket for an implantable medical device by forcing the tissue open. When rotated, the shape of the tunneler 104 may influence the shape of the pocket.

As shown in FIG. 1, the tunneler 104 may include a central portion 112 of the tunneler 104 having a greater width than end portions 114, 116 of the tunneler 104. The central portion 112, in certain instances, may have a width equal to, or at least approximately equal to, a width of the medical device. In addition, the central portion 112 may include a width that is 1%, 5%, 10%, 15%, 20%, 25%, 30%, 35%, 40%, 45%, or 50% (or any percentage in between) greater than a width of the end portions 114, 116. In addition, the tunneler 104 may include a distal tip 118, which may facilitate movement of the tunneler 104 through the tissue of a patient. The distal tip 118 may include a taper such that a depth or thickness of the distal tip 118 decreases from the end portions 114 toward an end of the distal tip 118 of the tunneler 104. In addition, the distal tip 118 may include a depth that is less than a depth of the central portion 112 and a depth of end portions 114, 116 of the tunneler 104.

Figure 2A:
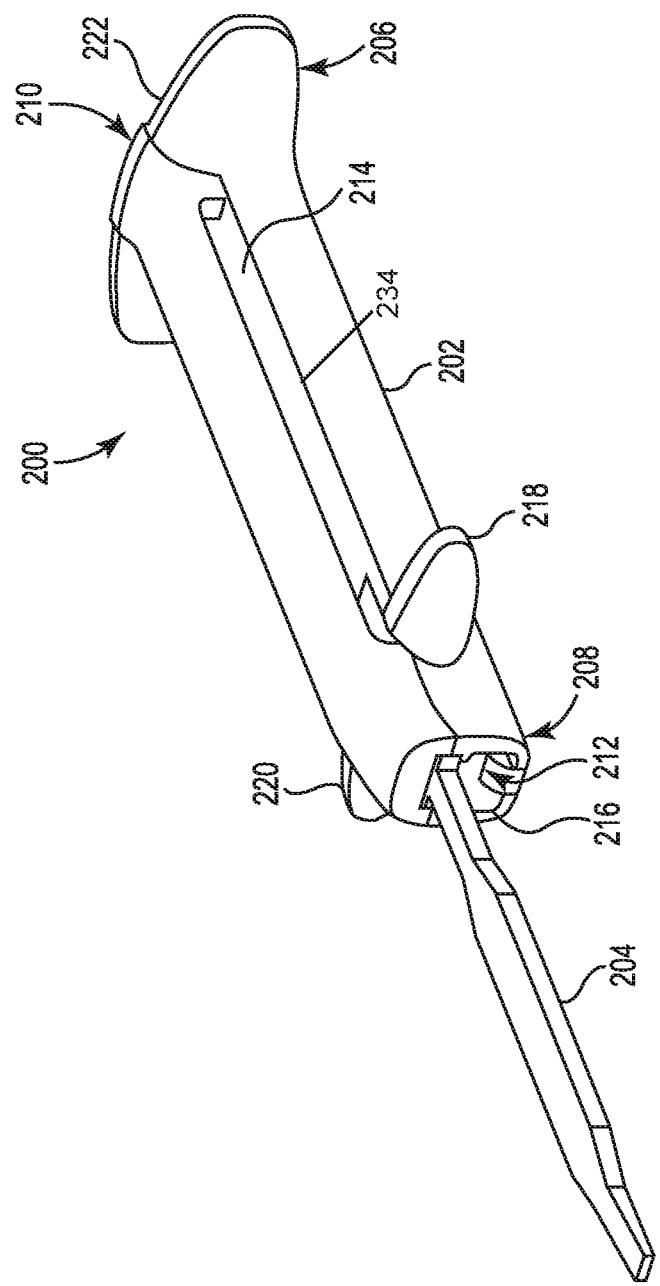
FIG. 2A is a perspective view of another illustrative introducer apparatus for facilitating subcutaneous implantation of a medical device, in accordance with embodiments of the disclosure.

FIG. 2A is a perspective view of another illustrative introducer apparatus 200 for facilitating subcutaneous implantation of a medical device, in accordance with embodiments of the disclosure. The introducer apparatus 200 includes a housing 202 having a proximal end 206 and a distal end 208. The proximal end 206 of the housing 202 may include a proximal opening 210, and the distal end 208 of the housing 202 may include at least one distal opening 212. Each of the housing 202, the proximal opening 210, and the distal opening 212 may be formed or manufactured to accommodate medical devices of various sizes. Further, the implantable medical device may be loaded into the housing 202 via either of the proximal opening 210 or the distal opening 212.

The introducer apparatus 200 may also include a tunneler 204. The tunneler 204 is arranged at the distal end 208 of the housing 202 and extends distally of the housing 202. In certain instances, the tunneler 204 may extend through the distal opening 212. The tunneler 204 may be configured to form a subcutaneous pocket for the medical device. In addition, the tunneler 204 may be moveable relative to the housing 202. More specifically, the housing 202 may include a first channel 214 extending along a length of the housing 202 from the distal opening 212. The tunneler 204 may be configured to move within the first channel 214. Further, the tunneler 204 may move within the first channel 214 toward the proximal end 206 of the housing 202. In certain instances, the first channel 214 may include lateral openings 234 (e.g., one opening shown in FIG. 2A with a matching opening on an opposing side of the housing 202). The lateral openings 234 may extend along a portion of the length of the housing 202 and correspond to the first channel 214, or the lateral openings 234 may correspond to the first channel 214 and similarly extend along the length of the housing 202. Further, the tunneler 204 may include gripping portions 218, 220 coupled thereto and extending laterally through the lateral openings 234. The gripping portions 218, 220 may be configured to facilitate movement of the tunneler 204 within the first channel 214. More specifically, the gripping portions 218, 220 provide external gripping surfaces for a user to apply force and thus translate the tunneler 204 within the housing 202.

The housing 202 may also include a handle 222 arranged at the proximal end 206 of the housing 202. The handle 222 provides a gripping surface for a user to manipulate the introducer apparatus 200. In addition, a medical device (shown in FIG. 2C) may be loaded into the housing 202 using the proximal opening 210. As discussed with reference to FIGS. 2B-2C, an inserter 205 may be provided with the introducer apparatus 200, which may extend through both the proximal opening 210 and the distal opening 212 of the housing 202. As a result and in certain instances, the inserter 205 may be configured to pass the medical device (shown in FIG. 2C) through the distal opening 212 of the housing 202.

FIG. 2B is a perspective view of the illustrative introducer apparatus 200, as shown in FIG. 2A, in an initial configuration and including an inserter 205, in accordance with embodiments of the disclosure. The inserter 205 may extend through both the proximal opening 210 and the distal opening 212 of the housing 202. As shown, the inserter 205 extends through the distal opening 212 adjacent to the tunneler 204. In certain instances, the distal opening 212 may include two or more separate openings with the inserter 205 and the tunneler 204 each extending through a different opening. The inserter 205 may be configured to pass the medical device (shown in FIG. 2C) through the distal opening 212 of the housing 202. The inserter 205 may include a handle portion 224 to provide a gripping surface for the user to manipulate and move the inserter 205 within the housing. The handle portion 224 of the inserter 205 may have a similar width as compared to a width of the handle 222 of the housing 202. In other instances, the handle portion 224 of the inserter 205 may have a greater or smaller width than a width of the handle 222 of the housing 202

Both the medical device (shown in FIG. 2C) and the inserter 205 may be configured to move within a second channel 216 (shown in FIG. 2B). The second channel 216 may extend between the proximal opening 210 and the distal opening 212 along a length of the housing 202. As a result, the tunneler 204 is configured to move within the first channel 214, and the inserter 205 is configured to move within the second channel 216. The first channel 214 and the second channel 216 are both internal to the housing 202. In addition, the first channel 214 and the second channel 216 may have the same length along the housing 202, the first channel 214 may have a shorter length than the second channel 216, or the first channel 214 may have a greater length than the second channel 216. Further, the first channel 214 may be laterally offset from the second channel 216 within the housing as is illustrated by the tunneler 204 being laterally offset from the second channel 216 in FIG. 2B.

In the initial configuration of the introducer apparatus 200, as shown in FIG. 2B, the tunneler 204 is in a fully-extended position through the distal opening 212 of the housing 202. In certain instances, the tunneler 204 is inserted/tunneled through an incision in a patient. Making the incision and using the tunneler 204 to form a pocket within a patient may be steps in a method of implanting a medical device using the introducer apparatus 200. The tunneler 204 may be tunneled or forced through tissue beneath the incision in order to create a pocket for implanting the medical device. In addition, the inserter 205, in the initial configuration of the introducer apparatus 200, may be in a fully-extended position away from the housing 202. In addition, and as shown in comparing FIGS. 2A and 2B, the inserter 205 may be distinct from and configured to disengage from the housing 202. The inserter 205 may be disengaged from the housing 202 (as shown in FIG. 2A) by moving the inserter 205 further away from the housing 202 along the second channel 216 in the fully-extended position.

FIG. 2C is a perspective view of the illustrative introducer apparatus 200, as shown in FIGS. 2A-B, in a first configuration, in accordance with embodiments of the disclosure. As shown in FIG. 2C, the inserter 205 has been moved (by the user) toward the housing 202 along the second channel 216 from the initial configuration shown in FIG. 2B. In the first configuration, a distal end 226 of the inserter 205 extends past the distal end 208 of the housing and through the distal opening 212. In certain instances, the medical device 228, loaded into the housing 202 through the proximal opening 210 in the initial configuration shown in FIG. 2A, may be ejected from the distal opening 212 of the housing 202 via the inserter 205. In addition, at least one end portion 230 of the medical device 228 may correspond or mirror the distal end 226 of the inserter 205. In these such instances, the distal end 226 of the inserter 205 may provide a surface that aids in positioning of the medical device 228 in the patient. The handle portion 224 of the inserter 205 may act as a stopping point such that the inserter 205 extends a fixed amount through the proximal opening 210 and the distal opening 212 of the housing 202. The handle portion 224 of the inserter 205 may contact the handle 222 of the housing 202. Positioning of the medical device 228 in the patient may be a step in a method of implanting a medical device using the introducer apparatus 200.

As noted previously with reference to FIG. 2B and the initial configuration, the tunneler 204 is provided through the incision in the patient to form the pocket. In the first configuration, the introducer apparatus 200 and the tunneler 204 is positioned within the formed pocket and extends distally of the housing 202. In transitioning the inserter 205 between the initial configuration and the first configuration while the tunneler 204 is in the patient, the medical device 228 may be ejected from the distal opening 212 of the housing 202 via the inserter 205 and positioned within the pocket created by the tunneler 204.

Figure 2E:
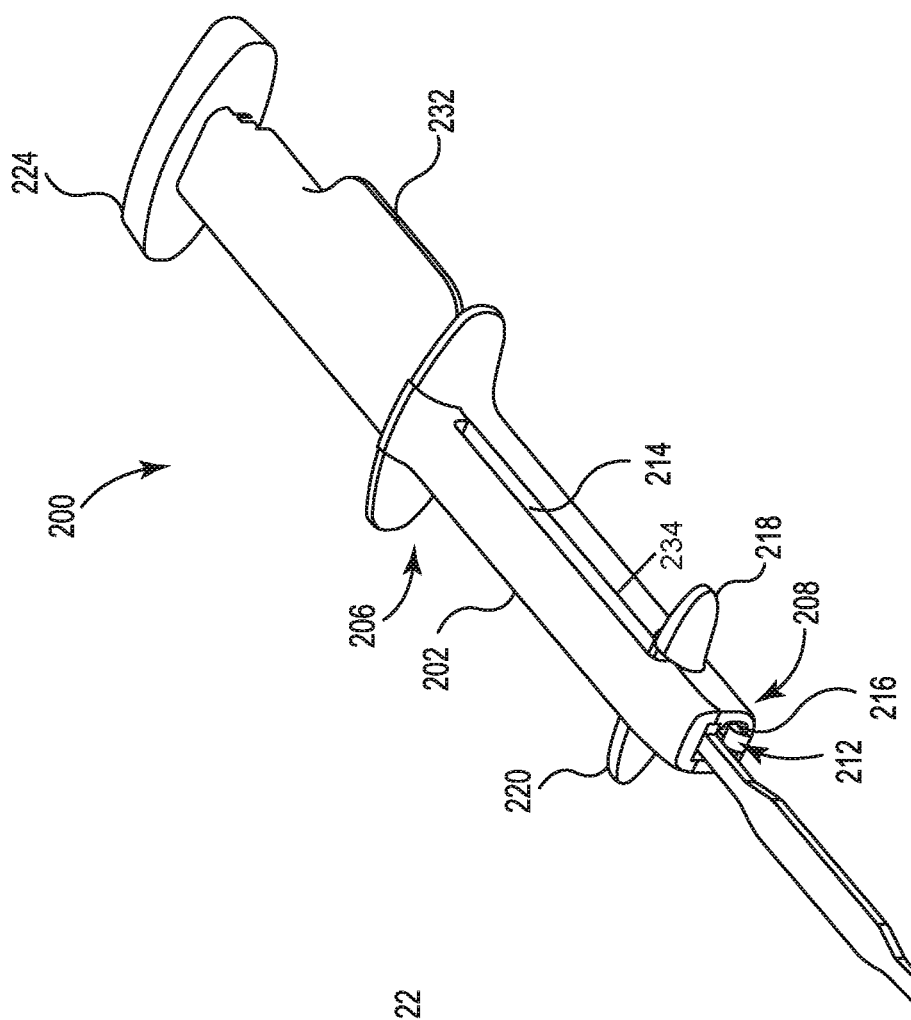
FIG. 2E is a perspective view of the illustrative introducer apparatus, as shown in FIGS. 2A-D, in the initial configuration with a locking structure, in accordance with embodiments of the disclosure.
Figure 2D:
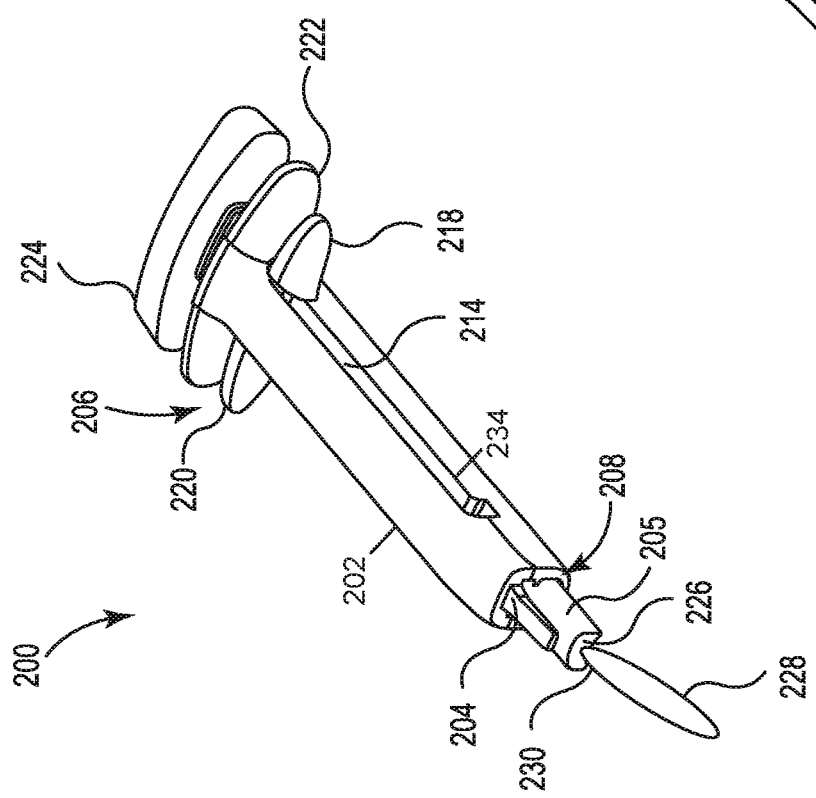
FIG. 2D is another perspective view of the illustrative introducer apparatus, as shown in FIGS. 2A-C, in a second configuration, in accordance with embodiments of the disclosure.

FIG. 2D is a perspective view of the illustrative introducer apparatus 200, as shown in FIGS. 2A-C, in a second configuration, in accordance with embodiments of the disclosure. In the second configuration, the inserter 205 remains in the same position as in the first configuration, and the tunneler 204 may be moved or retracted into the housing 202 along the first channel 214 through the distal opening 212. The tunneler 204 may be moved or retracted into the housing 202 via the gripping portions 218, 220. In instances where the introducer apparatus 200 is used to implant the medical device 228 in the body of a patient, the inserter 205 may hold the medical device 228 in the pocket created by the tunneler 204 as the tunneler 204 is moved or retracted into the housing 202. In certain instances, for example, removing an introducer apparatus after implantation of a medical device (e.g., an introducer that does not include the tunneler 204 that is moveable with respect to the housing 202) may frictionally engage the implanted medical device and alter its positioning. As a result, the implanted medical device may be removed/ejected from the patient while the introducer apparatus is being removed. The tunneler 204 being moveable with respect to the housing 202 assists in maintaining the position of the medical device 228 within the created pocket.

Retracting the tunneler 204 into the housing 202 and using the inserter 205 to maintain the medical device 228 in the pocket created by the tunneler 204 may be a step in a method of implanting a medical device using the introducer apparatus 200.

FIG. 2E is a perspective view of the illustrative introducer apparatus 200, as shown in FIGS. 2A-D, in the initial configuration with a locking structure 232, in accordance with embodiments of the disclosure. The locking structure 232 may lock the inserter 205 in the configuration (shown in FIG. 2B) such that the inserter 205 is not inadvertently moved. The locking structure 232 may surround a portion of the inserter 205, and be positioned between the handle portion 224 of the inserter 205 and the handle 222 of the housing 202. Removing the locking structure 232 may be a step in a method of implanting a medical device using the introducer apparatus 200.

The illustrative components shown in FIGS. 2A-E are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in FIGS. 2A-E may be, in embodiments, integrated with various other components depicted therein (and/or components not illustrated), all of which are considered to be within the ambit of the disclosed subject matter. For example, the tunneler 204 may include portions having a greater width other portions of the tunneler 204 (as shown and discussed with reference to FIG. 1).

Figure 3A:
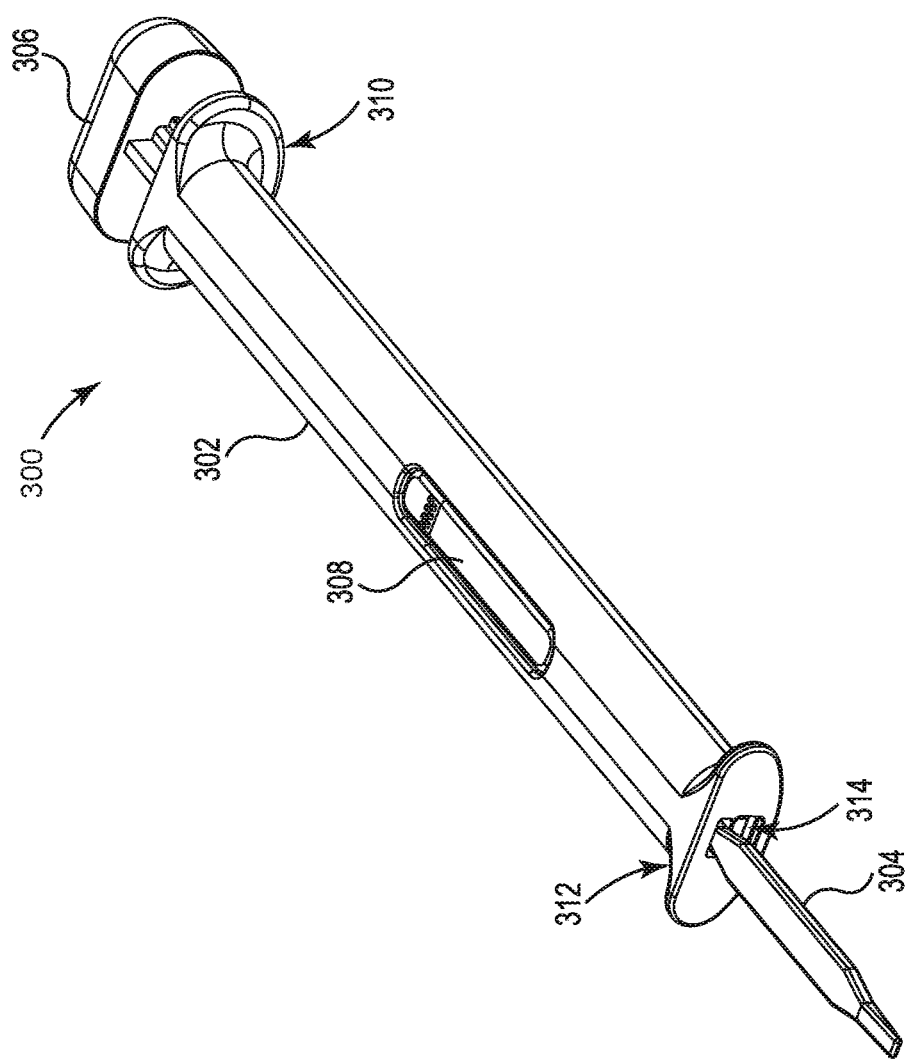
FIG. 3A is a perspective view of another illustrative introducer apparatus for facilitating subcutaneous implantation of a medical device, in accordance with embodiments of the disclosure.

FIG. 3A is a perspective view of another illustrative introducer apparatus 300 for a medical device 308, in accordance with embodiments of the disclosure. The introducer apparatus 300 shown in FIGS. 3A-E includes a housing 302, a tunneler 304, and an inserter 306. In addition, the housing 302 includes a proximal end 310 and a distal end 312. Each of the proximal end 310 and the distal end 312 includes an opening. As shown in FIG. 3A, the distal end 312 may include a distal opening 314. The inserter 306 may be configured to pass the medical device 308 through the distal opening 314 of the housing 302. In addition, the tunneler 304 may be extends distally of the housing 302 and may be configured to form a subcutaneous pocket for the medical device 308. In certain instances, the tunneler 304 may extend through the distal opening 314 of the housing 302. Further, the tunneler 304 may be configured to be moveable relative to the housing 302.

Figure 3B:
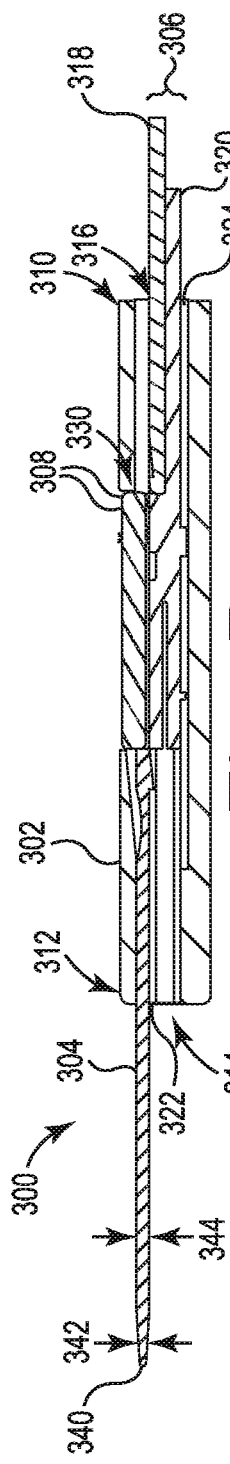
FIG. 3B is a cross-sectional side view of the illustrative introducer apparatus, as shown in FIG. 3A, in a loading configuration, in accordance with embodiments of the disclosure.

FIG. 3B shows a cross-sectional side view of the illustrative introducer apparatus 300, as shown in FIG. 3A, in a loading configuration, in accordance with embodiments of the disclosure. The housing 302 includes a proximal end 310 and a distal end 312. Each of the proximal end 310 and the distal end 312 of the housing 302 may include, respectively, a distal opening 314 and a proximal opening 316. The distal opening 314 (and the housing 302) may be formed or manufactured to accommodate medical devices of various sizes.

The housing 302 includes a first channel 322 and a second channel 324. Each of the first channel 322 and the second channel 324 extend along a length of the housing 302. The first channel 322 may extend from the distal opening 314, and the second channel 324 may extend between the distal opening 314 and the proximal opening 316. Further, the tunneler 304 is configured to move within the first channel 322, and the inserter 306 is configured to move within the second channel 324. The first channel 322, as is shown in FIG. 3B, may be laterally offset from the second channel 324. In addition, both the tunneler 304 and the inserter 306 extend through the distal opening 314. The tunneler 304 and the inserter 306 are adjacent to one another. In certain instances, the distal opening 314 may include two or more separate openings with the tunneler 304 and the inserter 306 each extending through a different opening.

In certain instances, the inserter 306 may include a first portion 318 and a second portion 320. The first portion 318 may be configured to contact, engage and/or connect with the second portion 320. In certain instances, each of the first portion 318 and the second portion 320 move within the second channel 324.

As noted above, the tunneler 304 may be configured to be moveable relative to the housing 302. The tunneler 304 may move within the first channel 322. In the loading configuration shown in FIG. 3B, the tunneler 304 extends through the distal opening 314 of the housing 302. In addition and as discussed in further detail below with reference to FIGS. 3D-E, the tunneler 304 may be configured to move as a result of being engaged with and/or connected to the first portion 318 of the inserter 306. The tunneler 304 may also include a distal tip 340. The distal tip 340 may have a depth 342 that is less than a depth 344 of remaining section of the tunneler 304. In addition, the distal tip 340 may have a taper such that the depth 342 lessens at a constant rate from the depth 344 of the remaining section of the tunneler 304. In creating the subcutaneous pocket in a patient, an incision may be made in the patient's skin. The incision may be made by a separate device, such as a scalpel. After the incision is made, the tunneler 304 may be inserted/tunneled through the incision in the patient. The depth 342 of the distal tip 340 may facilitate movement of tissue around the tunneler 304 in reaching a desired depth under the patient's skin. Making the incision and using the tunneler 304 to form a pocket within a patient may be steps in a method of implanting a medical device using the introducer apparatus 300.

The introducer apparatus 300 also may include a compartment 330 within the housing 302 configured to releasably hold the medical device 308. The compartment 330 may have a similar (or at least approximately similar) length, width, and/or depth to the medical device 308. As a result of the compartment having an approximately similar length, width, and/or depth to the medical device 308, surfaces of the compartment 330 may frictionally engage the medical device 308 to hold the medical device 308 within the compartment 330. The medical device 308 is shown in a loading configuration in FIG. 3B. In certain instances, the medical device 308 may be displaced from the compartment 330 as a result of the second portion 320 of the inserter 306 moved within the second channel 324 to a first configuration as shown in FIG. 3C.

Figure 3C:
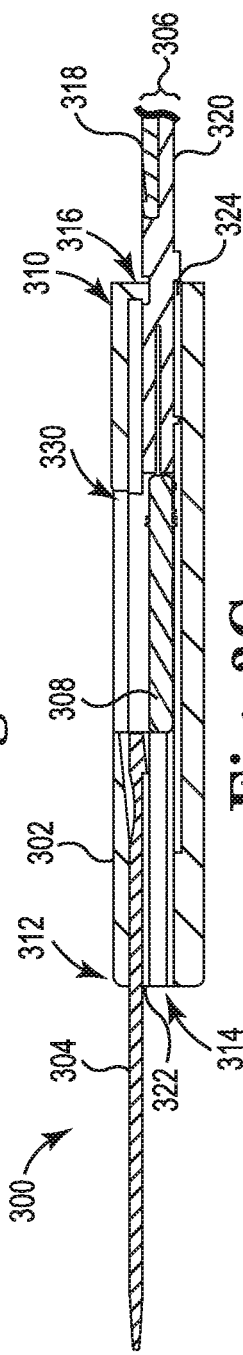
FIG. 3C is a cross-sectional side view of the illustrative introducer apparatus, as shown in FIGS. 3A-B, in a first configuration, in accordance with embodiments of the disclosure.

FIG. 3C shows a cross-sectional side view of the illustrative introducer apparatus 300, as shown in FIGS. 3A-B, in a first configuration, in accordance with embodiments of the disclosure. In the first configuration, the inserter 306 is moved proximally relative to the proximal opening 316 of the housing 302. Both the first portion 318 and the second portion 320 are moved proximally in transitioning from the loading configuration (shown in FIG. 3B) to the first configuration. As shown in FIG. 3C, the first portion 318 of the inserter 306 is configured to engage and/or connect with the second portion 320 of the inserter 306 to move the first portion 318 and the second portion 320 together within the second channel 324 in the first configuration.

The medical device 308 is releasably held within the compartment 330 in a loading configuration, as shown in FIG. 3B. In addition, the first portion 318 of the inserter 306 may be configured to retract the second portion 320 of the inserter 306 to move the first portion 318 and the second portion 320 together toward the proximal opening 316 from the loading configuration. Movement of the first portion 318 and the second portion 320 together toward the proximal opening 316 releases or drops the medical device 308 from the compartment 330 into the second channel 324. In certain instances, a user of the introducer apparatus 300 may apply force to the medical device 308 to release the medical device 308 from the compartment 330 into the second channel 324. In other instances, the lack of the second portion 320 of the inserter 306 being present in the second channel 324 will release the medical device 308 from the compartment 330 into the second channel 324. As shown in FIG. 3C, the tunneler 304 extends through the distal opening 314 in the first configuration. Moving/retracting the first portion 318 and the second portion 320 of the inserter 306 and releasing the medical device 308 from the compartment 330 may be steps in a method of implanting a medical device using the introducer apparatus 300.

Figure 3D:
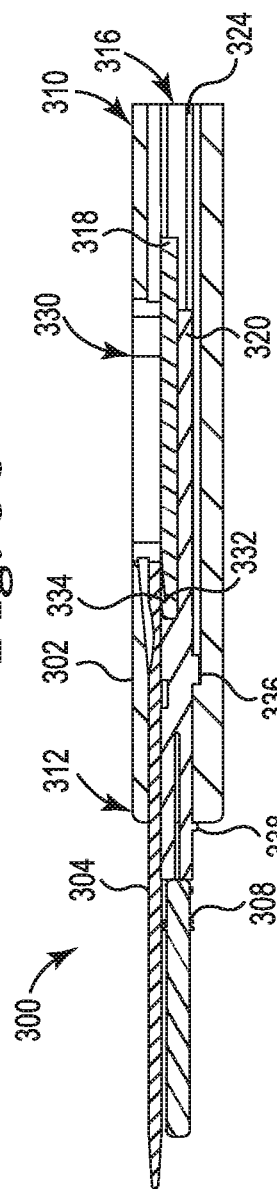
FIG. 3D is a cross-sectional side view of the illustrative introducer apparatus, as shown in FIGS. 3A-C, in a second configuration, in accordance with embodiments of the disclosure.

FIG. 3D shows a cross-sectional side view of the illustrative introducer apparatus 300, as shown in FIGS. 3A-C, in a second configuration, in accordance with embodiments of the disclosure. In the second configuration, the first portion 318 of the inserter 306 is configured to extend the second portion 320 of the inserter 306 through the distal opening 314. A user may apply force to the inserter 306 to move the first portion 318 and thereby move the second portion 320 of the inserter 306 along the second channel 324. In certain instances where the medical device 308 had been released from the compartment 330 into the second channel 324, extending the second portion 320 of the inserter 306 through the distal opening 314 also moves the medical device 308 along the second channel 324 and through the distal opening 314.

In certain instances, the second portion 320 of the inserter 306 includes at least one depth limiter 336, 338 configured to lock the second portion 320 of the inserter 306 within the distal opening 314 in the second configuration. The depth limiter 336, 338 may also provide a stopping point such that the section portion 320 of the inserter 306 extends a fixed amount through the distal opening 314 of the housing 302.

In addition, the first portion 318 of the inserter 306 is configured to engage and/or connect with the tunneler 304 in the second configuration. More specifically, each of the first portion 318 of the inserter 306 and the tunneler 304 includes snap-fit portions 332, 334. The snap-fit portions 332, 334 engage and/or connect with one another when the first portion 318 of the inserter contacts the tunneler 304 (e.g., in the second configuration).

As noted previously with reference to FIG. 3B, the tunneler 304 is provided through the incision in the patient to form the pocket. As a result, transitioning the inserter 306 to the second configuration may include ejecting the medical device 308 into the pocket created by the tunneler 304. Thus, ejecting the medical device 308 may include ejecting the medical device 308 and positioning the medical device 308 within the pocket. As result, moving the first portion 318 (and thereby moving the second portion 320) of the inserter 306, ejecting the medical device 308, and engaging the first portion 318 of the inserter 306 with the tunneler 304, as described with reference to FIG. 3D, may be steps in a method of implanting a medical device using the introducer apparatus 300.

Figure 3E:
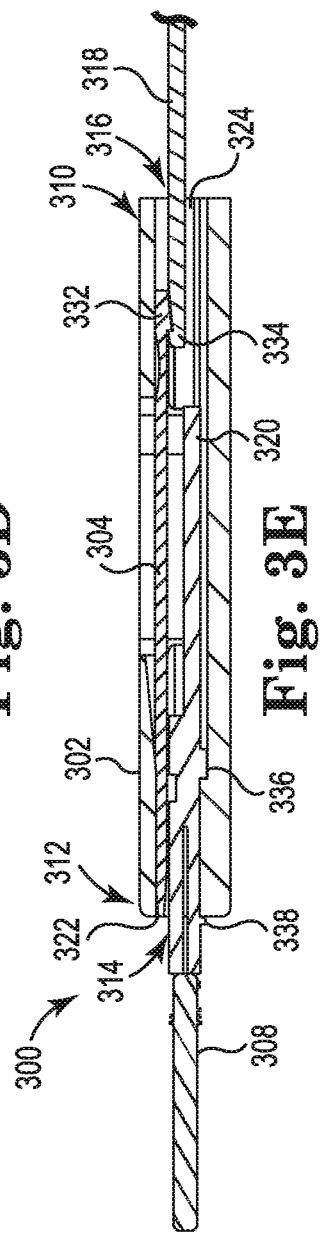
FIG. 3E is a cross-sectional side view of the illustrative introducer apparatus, as shown in FIGS. 3A-D, in a third configuration, in accordance with embodiments of the disclosure.

FIG. 3E shows a cross-sectional side view of the illustrative introducer apparatus 300, as shown in FIGS. 3A-D, in a third configuration, in accordance with embodiments of the disclosure. As shown in FIG. 3E, the medical device 308 is ejected from the housing 302. In addition, the second portion 320 of the inserter 306 extends through the distal opening 314 of the housing 302. Transitioning between the second configuration, shown in FIG. 3D, and the third configuration, includes retracting the tunneler 304 from the distal opening 314 along the first channel 322. Engagement and connection of the snap-fit portions 332, 334 of the first portion 318 of the inserter 306 and the tunneler 304 allows for movement of the first portion 318 of the inserter 306 to also move the tunneler 304. The depth limiter 336, 338 holds the second portion 320 of the inserter 306 in place during retraction of the first portion 318 of the inserter 306 and the tunneler 304. The tunneler 304 may be fully or partially retracted within the housing 302 through movement of the first portion 318 of the inserter 306 in a proximal direction.

In instances where the introducer apparatus 300 is used to implant the medical device 308 in the body of a patient, the second portion 320 of the inserter 306 may hold the medical device 308 in the pocket created by the tunneler 304 as the tunneler 304 is moved or retracted via the first portion 318 of the inserter 306. In certain instances, for example, removing an introducer apparatus after implantation of a medical device (e.g., an introducer that does not include the tunneler 304 that is moveable with respect to the housing 302) may frictionally engage the implanted medical device and alter its positioning. As a result, the implanted medical device may be removed/ejected from the patient while the introducer apparatus is being removed. The tunneler 304 being moveable with respect to the housing 302 assists in maintaining the position of the medical device 308 within the created pocket.

Retracting the tunneler 304 (and the first portion 318 of the inserter 306) and using the inserter 306 to maintain the medical device 308 in the pocket created by the tunneler 304 may be a step in a method of implanting a medical device using the introducer apparatus 300.

The illustrative components shown in FIGS. 3A-E are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in FIGS. 3A-E may be, in embodiments, integrated with various other components depicted therein (and/or components not illustrated), all of which are considered to be within the ambit of the disclosed subject matter. For example, the inserter 306 may include a handle portion 224 (as shown and discussed with reference to FIG. 2B) or the tunneler 304 includes portions having a greater width than other portions of the tunneler 304 (as shown and discussed with reference to FIG. 1).

FIG. 4A is a perspective view of another illustrative introducer apparatus 400 for a medical device (not shown), in accordance with embodiments of the disclosure. The introducer apparatus 400 includes a housing 402, a tunneler 404, and an inserter 406. The housing 402 includes a proximal end 408 and a distal end 412. Each of the proximal end 408 and the distal end 412 of the housing 402 may include, respectively, a distal opening 414 and a proximal opening 410. The distal opening 414 (and the housing 402) may be formed or manufactured to accommodate medical devices of various sizes.

The tunneler 404 may extend from the distal end 412 of the housing 402. The tunneler 404 may be configured to form a subcutaneous pocket for the medical device. In creating the subcutaneous pocket in a patient, an incision may be made in the patient's skin. The incision may be made by a separate device, such as a scalpel. After the incision is made, the tunneler 404 may be manipulated within the patient through the incision. In certain instances, the user may rotate the introducer apparatus 400 to create the pocket for an implantable medical device by forcing the tissue open. The shape of the tunneler 404 will influence the shape of the pocket.

The inserter 406 may be configured to be moveable relative to the housing 402 through both the proximal opening 410 and the distal opening 414. The inserter 406 may include a first handle portion 416 and a second handle portion 418 that assist a user in moving the inserter 406 through the proximal opening 410 and the distal opening 414. The inserter 406 may also include a distal end portion 424 that corresponds to or mirrors a surface of a medical device (not shown). The distal end portion 424 may enable the inserter 406 to hold the medical device in position by cupping the edges of the medical device. The medical device may be loaded within the housing 402 through either of the proximal opening 410 and the distal opening 414. In use, after the medical device is loaded within the housing 402, and after the tunneler 404 is used to create the pocket within the patient, the inserter 406 may move the medical device through the distal opening 414 and into the pocket. The housing 402 (and tunneler 404) may be removed from the pocket while maintaining the inserter 406 in place within the pocket. In certain instances, removing an introducer apparatus after implantation of a medical device (e.g., an introducer that does not include a moveable inserter 406 with respect to the housing 402) may frictionally engage the implanted medical device and alter its positioning. As a result, the implanted medical device may be removed/ejected from the patient while the introducer apparatus is being removed. The moveable inserter 406 assists in maintaining the position of the medical device within the created pocket.

Similar to the first handle portion 416 and the second handle portion 418, the housing 402 may also include a first handle portion 420 and a second handle portion 422. The first handle portion 420 and the second handle portion 422 may enable the user to facilitate movement of the housing 402.

Figure 4B:
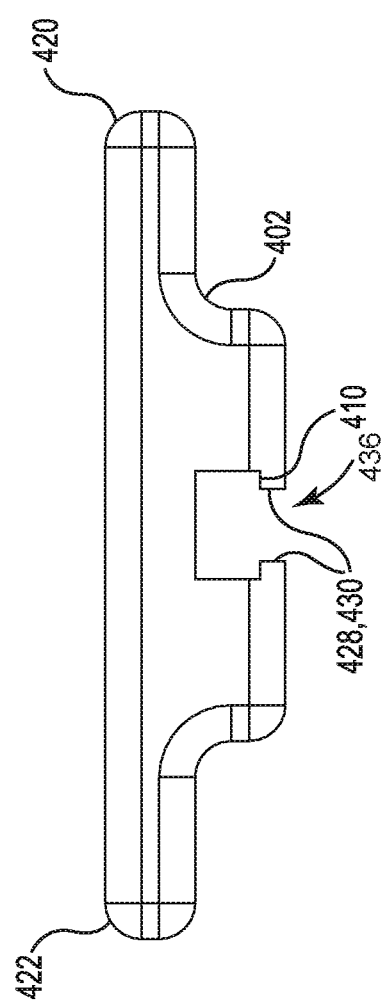
FIG. 4B is an end view of the illustrative introducer apparatus, as shown in FIG. 4A, in accordance with embodiments of the disclosure.

FIG. 4B shows an end view of the illustrative introducer apparatus 400, as shown in FIG. 4A, in accordance with embodiments of the disclosure. As shown in FIG. 4B, the housing 402 may include a first lateral extension 428 and a second lateral extension 430. The first lateral extension 428 and the second lateral extension 430 hold the inserter 406 lengthwise along a channel 436 between the proximal opening 410 and the distal opening 414 to enable linear movement of the inserter 406 therebetween.

The illustrative components shown in FIGS. 4A-B are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in FIGS. 4A-B may be, in embodiments, integrated with various other components depicted therein (and/or components not illustrated), all of which are considered to be within the ambit of the disclosed subject matter. For example, the tunneler 404 may have portions having a greater width than other portions of the tunneler 404 (as shown and discussed with reference to FIG. 1).

In certain instances, any of the illustrative introducer apparatuses described herein and an implantable medical device may be provided as a system. In addition to the introducer apparatus and the implantable medical device, the system may also include a device for making an incision in a patient. This device for making the incision (not shown) may be any device having a sharp edge (such as a scalpel). In addition, the incision may be made using a plunge cutter, or, for example, a vibratory plunge cutter as discussed in U.S. Provisional Patent No. 62/159,510, Titled "Vibratory Plunge Cutter," and herein incorporated by reference.

Figure 5:
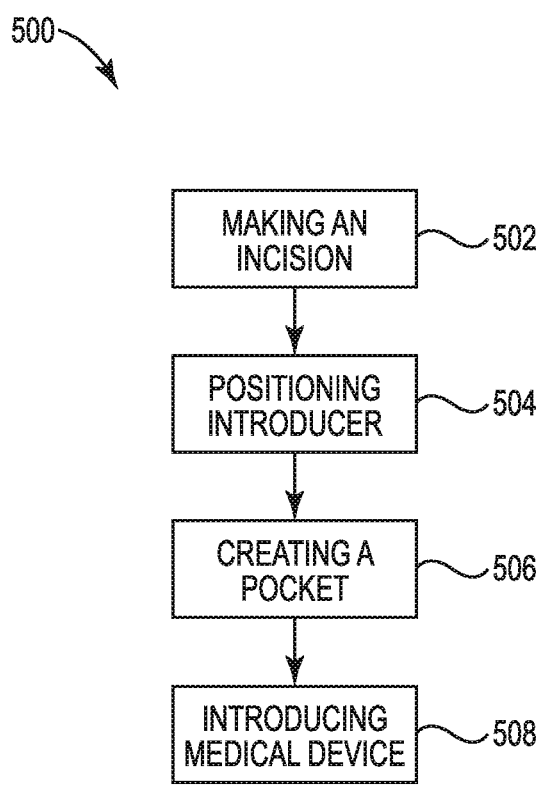
FIG. 5 is a flow diagram depicting an illustrative method of implanting an implantable medical device, in accordance with embodiments of the present disclosure.

FIG. 5 is a flow diagram 500 depicting an example method of implanting an implantable medical device in accordance with embodiments of the present disclosure. As is shown at block 502, the method includes making an incision in a patient's skin. After the incision is made and as is shown at block 504, the method includes positioning the introducer within the incision. The introducer may include a housing having a proximal end and a distal end and a distal opening at or adjacent the distal end. Further, the introducer may include a tunneler extending distally from the housing, and an inserter. The introducer as used in the method is shown in further detail with reference to any of FIGS. 1-4.

In addition and as is shown at block 506, the method includes creating a pocket in the tissue of the patient for the implantable medical device by using the tunneler. In certain instances, this may include inserting the tunneler within the patient via the incision. In certain instances, creating the pocket for the implantable medical device may include rotating the introducer apparatus. Further, as is shown at block 508, the method includes introducing the implantable medical device to the pocket within the patient by ejecting the implantable medical device via the inserter from the housing and through the distal opening and into the subcutaneous pocket. In certain instances, introducing the implantable medical device also includes retracting or removing one of the tunneler (e.g., as described with reference to FIG. 2 or FIG. 3) or inserter (e.g., as described with reference to FIG. 4) relative to the housing to remove the tunneler and/or the inserter from the pocket while leaving the medical device in the subcutaneous pocket. The method may include holding the medical device within the pocket using the inserter. The step of holding the medical device within the pocket using the inserter may occur during the step of removing the tunneler from the pocket.

Various modifications and additions can be made to the illustrative embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. An introducer apparatus for facilitating subcutaneous implantation of a medical device, the introducer apparatus comprising: a housing having a proximal end and a distal end, the housing defining at least one distal opening at or adjacent to the distal end; an inserter configured to pass the medical device through the at least one distal opening of the housing and to extend through a proximal opening and the at least one distal opening of the housing; and a tunneler configured to extend distally of the housing to form a subcutaneous pocket in tissue of a patient for implantation of the medical device, the tunneler being moveable relative to the housing and configured to retract in response to withdrawal of the inserter through engagement of snap-fit portions on the tunneler and the inserter after extension of the inserter through the distal opening of the housing.

2. The introducer apparatus of claim 1, wherein the housing comprises a first channel extending along a length of the housing proximally from the at least one distal opening, and a second channel extending between the proximal opening and the at least one distal opening along the length of the housing, and the tunneler is configured to move within the first channel, and the inserter is configured to move within the second channel.

3. The introducer apparatus of claim 2, wherein the inserter comprises a first portion and a second portion, the second portion being configured to engage the medical device and pass the medical device through the at least one distal opening of the housing.

4. The introducer apparatus of claim 3, wherein the first portion of the inserter is configured to engage the second portion of the inserter to move the second portion and the first portion together within the second channel in a first configuration, extend the second portion of the inserter through the at least one distal opening and engage a portion of the tunneler in a second configuration, and retract the tunneler from the at least one distal opening along the first channel in a third configuration.

5. The introducer apparatus of claim 4, further comprising a compartment within the housing configured to releasably hold the medical device.

6. The introducer apparatus of claim 5, wherein the medical device is releasably held within the compartment in a loading configuration, and the first portion of the inserter is configured to retract the second portion of the inserter to move the first portion and the second portion together toward the proximal opening from the loading configuration, and the medical device releases from the compartment into the second channel.

7. A system comprising: a medical device; and an introducer apparatus for facilitating subcutaneous implantation of the medical device, the introducer apparatus comprising: a housing having a proximal end and a distal end, and including at least one distal opening at or adjacent to the distal end, an inserter configured to pass the medical device through the at least one distal opening of the housing and to extend through a proximal opening and the at least one distal opening of the housing, and a tunneler configured to form a subcutaneous pocket for the medical device and extend distally of the housing for insertion of the medical device in a first configuration, and retract in response to withdrawal of the inserter relative to the first configuration in a second configuration through engagement of snap-fit portions on the tunneler and the inserter after extension of the inserter through the distal opening of the housing.

8. The system of claim 7, wherein the housing comprises a first channel extending along a length of the housing proximally from the at least one distal opening, and a second channel extending between the proximal opening and the at least one distal opening along the length of the housing, and the tunneler is configured to move within the first channel, and the inserter is configured to move within the second channel.

9. The system of claim 7, wherein the inserter comprises a first portion and a second portion, the second portion being configured to engage the medical device and pass the medical device through the at least one distal opening of the housing.

10. The system of claim 9, wherein the first portion of the inserter is configured to: engage the second portion of the inserter to move the second portion and the first portion together within the second channel in the first configuration, extend the second portion of the inserter through the at least one distal opening and engage a portion of the tunneler in the second configuration, and retract the tunneler from the at least one distal opening along the first channel in a third configuration.

11. The system of claim 7, further comprising a compartment within the housing configured to releasably hold the medical device.

12. The system of claim 7, wherein the tunneler comprises a central portion and end portions surrounding the central portion, wherein the central portion comprises a greater width than at least one of the end portions of the tunneler.

13. The system of claim 12, wherein the tunneler comprises a distal tip having a depth that is less than a depth of the central portion and the end portions of the tunneler.

* * * * *